US007141684B2

(12) United States Patent
Pews

(10) Patent No.: US 7,141,684 B2
(45) Date of Patent: Nov. 28, 2006

(54) DIEPOXIDE DERIVATIVES OF DIALLYL PHENOLICS

(76) Inventor: R. Garth Pews, 4830 Osprey Dr., South, Apt. 603, St. Petersburg, FL (US) 33711

( * ) Notice: Subject to any disclaimer, the term of this patent is extended or adjusted under 35 U.S.C. 154(b) by 348 days.

(21) Appl. No.: 10/693,531

(22) Filed: Oct. 24, 2003

(65) Prior Publication Data

US 2005/0090673 A1    Apr. 28, 2005

(51) Int. Cl.
*C07D 303/23* (2006.01)
(52) U.S. Cl. ...................................... 549/554
(58) Field of Classification Search ................. 549/554
See application file for complete search history.

(56) References Cited

U.S. PATENT DOCUMENTS 6,441,121 B1 * 8/2002 Musa et al. ................. 528/103
6,670,474 B1 * 12/2003 Pews .......................... 544/238

* cited by examiner

*Primary Examiner*—James O. Wilson
*Assistant Examiner*—Ebenezer Sackey
(74) *Attorney, Agent, or Firm*—Bernd W Sandt

(57) ABSTRACT

The present invention relates to the preparation of ethers and esters of diallylphenols and the epoxidation of the diallyl moiety to provide bis-epoxide ether and ester intermediates useful in the preparation of epoxy resins.

20 Claims, No Drawings

DIEPOXIDE DERIVATIVES OF DIALLYL PHENOLICS

BACKGROUND OF THE INVENTION

The Epoxy Intermediates and resins industry (Encyclopedia of Chemical Technology, Volume 9, Fourth Edition, John Wiley & Sons Page 370) is a multibillion dollar business that is based on the following technology that involves no less than ten chemical reactions.

Benzene+propylene→isopropyl benzene
Isopropyl benzene→cumene hydroperoxide
Cumene hydroperoxide→phenol+acetone
Phenol+acetone→"Bis-A" or ( Phenol+formaldehyde→"Bis-F")
Propylene+chlorine→allyl chloride
Allyl chloride+sodium hydroxide+chlorine→propylene chlorohydrins
Propylene chlorohydrins+sodium hydroxide→epichlorohydrin
Bis-A+epichlorohydrin+NaOH→"Bis-A glycidol ether"
Bis-A glycerol ether+Bis-A→epoxy resin
Sodium chloride+water→chlorine+sodium hydroxide Several aspects of the above reaction sequence have negative process implications with regards to yields, chlorinated byproducts, hydraulic load and biological hazards. These include but are not limited to the following: (a) benzene is a known carcinogen, (b) Bis-A is an endocrine disrupter (mimics estrogen). Recent research (Current Biology, Volume 13, page 546, 2003) has shown that abnormalities in developing mouse eggs occurred at levels of bisphenol A to which people are commonly exposed. Similar aberration in human eggs would lead to miscarriages and birth defects, and (c) chlorination of propylene to allyl chloride and the addition of hypochlorous acid to allyl chloride yield higher chlorinated byproducts resulting in ~⅓ pounds of chlorinated waste per pound of epichlorohydrin. In addition, the process requires a chlor-alkali facility, hence a local hence a local source of salt and huge volumes of water. The products and processes of the present invention ameliorate if not eliminate some of the disadvantages of prior art of epoxy products and processes.

BRIEF DESCRIPTION OF THE INVENTION

The present invention relates to the preparation of ethers and esters of diallylphenols and the epoxidation of the diallyl moiety to provide bis-epoxide ether and ester intermediates useful in the preparation of epoxy resins. The epoxy ethers and esters of carboxylic, carbonic, phosphoric and sulfuric acids of the present invention are represented by the following formulas:

$$CH_2CHCH_2\text{—}Ar\text{—}CH_2CHCH_2 \quad (I)$$
$$\underset{O}{\backslash/} \quad \underset{OR}{|} \quad \underset{O}{\backslash/}$$

$$CH_2CHCH_2\text{—}Ar\text{—}CH_2CHCH_2 \quad (II)$$
$$\underset{O}{\backslash/} \quad \underset{O\text{—}CO\text{—}R}{|} \quad \underset{O}{\backslash/}$$

$$CH_2CHCH_2\text{—}Ar\text{—}CH_2CHCH_2, \quad (III)$$
$$\underset{O}{\backslash/} \quad \underset{OCO\text{—}OR}{|} \quad \underset{O}{\backslash/}$$

-continued $$CH_2CHCH_2\text{—}Ar\text{—}CH_2CHCH_2, \quad (IV)$$
$$\underset{O}{\backslash/} \quad \underset{OSO_2R}{|} \quad \underset{O}{\backslash/}$$

$$CH_2CHCH_2\text{—}Ar\text{—}CH_2CHCH_2 \quad (V)$$
$$\underset{O}{\backslash/} \quad \underset{OPORR'}{|} \quad \underset{O}{\backslash/}$$

$$CH_2CHCH_2\text{—}Ar'\text{—}CH_2CHCH_2 \quad (VI)$$
$$\underset{O}{\backslash/} \quad \underset{\{OX\}_2}{|} \quad \underset{O}{\backslash/}$$

where Ar is a trivalent aromatic radical of 6–20 carbon atoms, Ar' is a bridged diaromatic radical having the formula Ar—Y—Ar and Y is O, CO, S, SO$_2$, —(CH$_2$)y , or —C(R")$_2$— and y is from 0 to 6, and R and R' are the same or different alkyl, aryl, alkylene aryl, arylene alkyl, alkylene alkoxy, alkylene aryloxy, arylene alkoxy and arylene aryloxy aryl, radicals having from 6–20 carbon atoms, X is —R, —COR, —COOR, —SO$_2$R, —PORR'and R" is methyl.

DETAILED DESCRIPTION OF THE INVENTION

The synthesis of diepoxides described in the present invention requires the introduction of the allylic moiety to the aromatic ring that is converted in a subsequent reaction to the 2,3-epoxypropyl moiety. The allylation of phenols is well documented in the literature utilizing allyl aryl ethers, that on heating, rearrange to allyl phenols. The reaction is called the Claison Rearrangement (Advanced Organic Chemistry, 3$^{rd}$ Edition, by J. March, John Wiley & Sons 1985). Allyl aryl ethers are readily prepared from the phenate salt and allyl derivatives.

$C_6H_5OH+CH_2=CHCH_2X+base\rightarrow C_6H_5OCH_2CH=CH_2$
where X=chloride, bromide, acetate, tosylate etc.
$C_6H_5OCH_2CH=CH_2+heat\rightarrow CH_2=CHCH_2\text{—}C_6H_5OH$ The preparation of the novel diepoxides described in the present invention utilizes the Claison rearrangement and the allyl ether synthesis in one of two ways depending on the structure of the aromatic substrate. If the starting aromatic is a monophenol, the allylation-rearrangement is carried out a second time to obtain the diallyl product as illustrated below for phenol.

Phenol+allyl chloride+base→allyl phenyl ether
Allylphenyl ether+heat+solvent→2-allyl phenol
2-allyl phenol+allyl chloride→2-allyl phenyl ether
2-allyl phenyl ether+heat+solvent→2,6-diallyl phenol The diallylphenol is derivatized to either the desired ether or ester and oxidized to the diepoxide with a peracid, hydrogen peroxide/catalyst, t-butyl hydroperoxide/catalyst system that are well documented in the literature. If the starting aromatic is a diphenol, the latter is diallylated to the bis ether and rearranged as described above to the diallyl diphenol. Derivatization to either a diether or diester as described above followed by oxidation yields the desired diepoxide. The latter process with diphenols is advantageous in that two process steps are eliminated (an allylation and a rearrangement). The following are examples of phenols and diphenols that may be used as starting materials for the invention: phenol, 4-methoxyphenol, 4-methylphenol, 2,6-dichlorophenol, 2-naphthol, 4-cyanophenol, 4-hydroxybiphenyl, 4-tert.butyl phenol, 4-dodecylphenol, 3-butoxyphenol, 3,5-dimethylphenol, 3-trifluoromethylphenol, 2,4-diethylphenol, catechol, hydroquinone, resorcinol, 2,2-(4-hydroxyphenyl)propane, 4,4'-sulfonyldiphenol, 4,4'-dihydroxybenzophenone, 4,4'-hydroxyphenylmethane, 4-hydroxyphenyl ether, 2-hydroxyphenylthioether, 4,4'dihydroxybiphenyl.

The condensation of the bis-epoxides of this invention with diphenols, e.g., bis-phenol-A, bis-phenol-F,4-hydroxyphenyl sulfone, 4,4* dihydroxybenzophenone, 4,4'dihydroxybiphenyl, and 1,4-(4-hydroxyphenyl)butane, with dicarboxylic acids, e.g., isophthalic acid, succinic acid and cyclohexane dicarboxylic acids, with amino phenols, e.g, 4-aminophenol, 4-amino-4*-hydroxyphenylether, and 4-amino-4'-hydroxybiphenyl, with hydroxycarboxylic acids, e.g., 4-hydroxybenzoic acid, and 6-hydroxy-2-naphthoic acid, with amino acids, e.g., 4-aminobenzoic acid, with diamines, e.g., 4,4'-diaminophenyl ether, 1,3-diaminobenzene and 1,3-diaminopropane or with disulfonamides, e.g., 1,3-benzenedisulfonic acid: bis-N-methylamide results in new and valuable epoxy resins for protective coatings, structural composites, electrical laminates and adhesives. The chemistry provides the opportunity to manufacture resins with fewer chemical transformations, less capital and a reduction in the waste load associated with the bis-A epichlorohydrin technology. The resins can be obtained from the bis-epoxides using condensation procedures known in the art. An example of a resin synthesis from readily available starting materials using the diepoxide route of the present invention is outlined below:
1. Toluene→phenol (T. Shikada, et al J. Chem. Soc., Chem. Commun, 1994)
2. Propylene→allyl acetate
3. Phenol+sulfuric acid→4,4'- sulfonyldiphenol
4. 4,4'-Sulfonyldiphenol→4-alloxyphenyl sulfone
5. 4-Alloxyphenyl sulfone→3-allyl-4-hydroxyphenyl sulfone
6. 3-Allyl-4-hydroxyphenyl sulfone→3-allyl-4-methoxyphenyl sulfone
7. 3-Allyl-4-methoxyphenyl sulfone→3- (2,3-epoxypropyl)-4-methoxyphenyl sulfone
8. 3- (2,3-Epoxypropyl)-4-methoxyphenyl sulfone+(diphenol, diacid, etc.,)→epoxy resin The following examples further illustrate novel epoxides of the present invention:

EXAMPLE 1

PREPARATION OF 2,6-DI(2,3-EPOXYPROPYL)ANISOLE 2,6-Diallylphenol was prepared via reacting 2-allylphenol with an allyl halide to form 2-allylphenyl ether. Refluxing the latter in o-dichlorobenzene for 24–48 hrs. gave 2,6-diallylphenol. The desired phenol was purified by distillation, bp 91–92 C(1 mm). MS m/z 174 (M+ calcd for $C_{12}H_{14}O=174$). H NMR (300 MHz, $CDCl_3$), d 3.48 (d, 4, $CH_2$), 5.15–5.38 (m, 4,vinyl), 5.98–6.18 (m, 2, CH vinyl), 6.85–7.15 (m, 3 aromatic). 2,6-Diallylphenol (5.2 g, 0.03 mol) was diluted with methanol (50 ml) and sodium hydroxide added to the phenol solution. Iodomethane (5.0 g, 0.03 mol.) was added to the solution and stirred overnight at room temperature. The methanol solution was diluted with water and the product extracted with hexane, dried over $MgSO_4$, filtered and evaporated to give 2,6-diallylanisole. MS m/z 188 (M+ calcd for $C_{13}H_{16}O=188$). H NMR (300 MHz, $CDCl_3$) d 3.45–3.55 (d, 4, $CH_2$), 3.60 (s, 3, $CH_3$), 5.10–5.20 (d, 4, $CH_2$), 6.00–6.16 (m, 2, CH vinyl), 7.07–7.20 (m, 3, aromatic). 2,6-Diallylanisole was oxidized with meta-chloro perbenzoic acid as follows: MCPBA (~70%, 5.73 g) was dissolved in dichloromethane (50 ml) and dried over $MgSO_4$. After filtration of the $MgSO_4$, 2,6-diallylanisole (1.88 g, 0.01 mol) was added to the MCPBA solution and stirred for 24–48 hrs. at room temperature. The precipitate, m-chlorobenzoic acid was filtered and, the dichloromethane solution washed with dilute sodium bisulfite and dilute potassium carbonate and dried over $MgSO_4$. After filtration of the $MgSO_4$, the dichloromethane was evaporated to give the liquid diepoxide, bp 138° C. (1 mm). MS m/z 220 (M+ calcd for $C_{13}H_{16}O_3=220$). H NMR (300 MHz, $CDCL_3$) d 2.60–2.70 (m, 2, $CH_2$ epoxypropyl), 2.75–3.10 (m, 6, $CH_2$ epoxypropyl), 3.25–3.50 (m, 2, CH epoxypropyl), 3.82 (s, 3, $OCH_3$), 7.05–7.25 (m, 1, aromatic), 7.40–7.60 (m, 2, aromatic).

EXAMPLE 2

PREPARATION OF 2,6-DI(2,3-EPOXYPROPYL) PHENYL ETHOXYETHYL ETHER 2,6-Diallylphenol (5.2 g, 0.03 mol) was diluted with 95% ethanol (50 ml). Sodium hydroxide (1.4 gm, 0.03 mol) was added to the phenol solution followed by 2-chloroethylether (3.8 gm, 0.035 mol). The reaction mixture was refluxed for 48 hrs, cooled, diluted with water, extracted with hexane and dried over $MgSO_4$. Filtration of the $MgSO_4$ and evaporation of the hexane gave 5.1 g of 2,6-diallylphenyl ethoxyethyl ether. MS m/z 246 (M+ calcd for $C_{16}H_{22}O_2=246$). H NMR (300 MHz, $CDCl_3$) d 1.30 (3, t, $CH_3$), 3.40–3.55 (4, m, $CH_2$ allyl), 3.65–3.75 (2,q, $OCH_2$ methyl), 3.80 (q, 2, $OCH_2$), 4.00(q, 2, $OCH_2$), 5.05–5.25 (m, 4, $CH_2$ vinyl), 5.90–6.20 (m, 2, CH vinyl), 7.05–7.20 (m, 4, $CH_2$ vinyl), 7.05–7.20 (m, 3, aromatic). Oxidation of the product as described in Example 1 gave 2,6-di-(2,3-epoxypropyl)phenyl ethoxyethyl ether as an oil. MS m/z 278 (M+ calcd for $C_{16}H22O_4=278$). H NMR (300 MHz, $CDCl_3$) d 1.25 (t, 3, $CH_30$, 2.65–2.85 (m, 4, epoxypropyl $CH_2$), 2.90–3.15 (m, 4, epoxypropyl $CH_2$), 3.21–3.35(m, 2, epoxypropyl CH), 3.65 (q, 2, $OCH_2$), 3.80 (q, 2, $OCH_2$), 4.00 (q, 2, $OCH_2$), 5.33 (s, 3, $OCH_3$), 7.05–7.33 (m, 3, aromatic).

EXAMPLE 3

PREPARATION OF 4-METHYL-2,6-di(2,3-EPOXYPROPYL)PHENYL METHYL ETHER

4-Methyl-2,6-diallylphenyl methyl ether was prepared from p-creosol as described for 2,6-diallylphenol in Example 1. MS m/z 202 (M+ calcd for $C_{14}H_{18}O_2=202$). H NMR(300 MHz, $CDCL_3$) d 2.35 (s, 3, $CH_3$), 3.45 (d, 4, $OCH_2$), 3.57 (s. 3, $OCH_3$), 5.10–5.29 (m, 4, $CH_2$ vinyl), 5.95–6.20 (m, 2, $CH_2$ vinyl), 6.95, (s, 2, aromatic). Oxidation of the product as described in Example 1 gave 4-methyl-2,6-di-(2,3-epoxypropyl) phenyl anisole as an oil. MS m/z 234. (M+ calcd for $C_{14}H_{18}O_4=234$). H NMR (300 MHz, $CDCL_3$) d 2.30 (s, 3, $CH_3$), 2.60 (d, 2, epoxypropyl), 2.80–3.00 (m, 6, epoxypropyl), 3.20–3.30 (m, 2, epoxypropyl), 3.75 (s, 3, $OCH_3$), 7.05 (s, 2, aromatic).

EXAMPLE 4

PREPARATION OF 2,6-DI(2,3-EPOXYPROPYL) PHENYL BENZYL ETHER 2,6-Diallylphenol (3.48 gm, 0.025 mol) was diluted with methanol (50 ml) and sodium hydroxide (0.8 gm 0.02 mol) was added to the solution followed by the benzyl chloride (3.60 gm, 0.2 mol.). The solution was refluxed for 2 hr, cooled, poured onto water and extracted with hexane. After washing with water and dilute sodium hydroxide, the organic layer was dried over $MgSO_4$, filtered and evaporated to give 2,6-diallylphenyl benzyl ether. MS m/z 264 (M+ calcd for $C_{19}H_{20}O$=264). H NMR (300 MHz, $CDCL_3$) d 3.45–3.55 (d, 4, $CH_2$ allyl), 4.85 (s, 2, $CH_2$ benzyl), 5.05–5.20 (m, 4, $CH_2$ vinyl), 5.96–6.15 (m, 2, CH vinyl), 7.10–7.25 (m, 3, aromatic), 7.35–7.70 (m, 5, aromatic). Oxidation of the product as described in Example 1 gave 2,6-di(2,3-epoxyypropyl) phenyl benzyl ether as an oil. MS m/z 296 (M+ calcd for $C+H_{20}O_3$=296). H NMR (300 MHz, $CDCl_3$) d 2.60–2.70 (m, 2, $CH_2$ epoxypropyl), 2.75–3.10 (m, 6, $CH_2$ epoxypropyl), 2.31–2.46 (m, 2, $CH_2$ epoxypropyl), 4.75 (s, 2, $CH_2O$), 7.10–7.25 (m, 1, aromatic) 7.45–7.60 (m, 2, aromatic), 7.60–8.15 (m, 5, aromatic).

EXAMPLE 5

PREPARATION OF 2,6-(2,3-EPOXYPROPYL) PHENYL-4-CYANOPHENYL ETHER 2,6-Diallylphenol (3.8 gm, 0.02 mol) was oxidized with m-chloroperbenzoic acid as described in Example 1 to give 2,6-di(2,3-epoxypropyl)phenol. MS m/z 206 (M+ calcd for $C_{12}H_{14}O_3$=206). H NMR (300 MHz, $CDCl_3$) d 2.65 (d, 2, $CH_2$ epoxypropyl) 2.75–2.96 ($CH_2$ epoxypropyl), 3.12 (d, 2, CH epoxypropyl), 3.25–3.35(m, 2, CH epoxypropyl), 6.80 (t, 1, aromatic), 7.10 (d, 2, aromatic). The product 2,6-di(2,3-epoxypropyl)phenol was diluted with dimethylacetamide (50 ml) and neutralized with sodium hydroxide. 4-Fluorobenzonitrile (1 equivalent of the phenol) was added and the mixture heated and stirred overnight at 50° C. After cooling, the reaction was diluted with ethyl acetate and washed with water (4×), dried over $MgSO_4$ and evaporated to give 2,6-di(2,3epoxypropyl)phenyl 4-cyanophenyl ether. MS m/z 307 (M+ calcd for $C_{19}H_{17}O_3N$=307). H NMR (300 MHz, $CDCl_3$) d 2.50, (d, 2, $CH_2$ epoxypropyl $CH_2$), 2.65–2.90 (m, 4, $CH_2$ epoxypropyl), 3.15–3.30 (m, 2, $CH_2$ epoxypropyl), 3.45–3.75 (m, 2, epoxypropyl CH), 6.75–7.06 (m, 3, aromatic), 7.00–7.75 (m, 4, aromatic).

EXAMPLE 6

PREPARATION OF 2,6-DI(EPOXYPROPYL)PHENYL OCTADECYL ETHER

Diallylphenol (3.48 gm, 0.02 mol) was diluted in dimethyl sulfoxide (50 ml) and sodium hydroxide (0.8 gm, 0.02 mol) added to the solution followed by 1-chlorooctadecane (5.78 gm, 0.02 mol) and heated at 80 C. for 2 hrs. After cooling and diluting with water, the reaction mixture was extracted with hexane, dried over $MgSO_4$ filtered and evaporated to give the desired product. MS m/z 426. (M+ calcd for $C_{30}H_{50}O$=426). H NMR (300 MHz, $CDCl_3$) d 0.80 (t ,3, $CH_3$), 1.25 (s, 32, $CH_2$).1.75–1.80 (m, 2, $CH_2$), 3.30–3.40 (d, 4, $CH_2$), 3.70–3.80 (t, 2, $OCH_2$), 5.05–5.21(m, 2, $CH_2$ vinyl), 5.95–6.10 (m, 2,$CH_2$ vinyl), 7.00–7.20(m, 3, aromatic). Oxidation with MCPBA as described in Example 1 gave 2,6-di(epoxypropyl)phenyl octadecyl ether. MS m/z 458 (M+ calcd for $C_{30}H_{50}O_3$=458). H NMR (300 MHz, $CDCl_3$) d 0.80 (t, 3, $CH_3$), 1.25 (s, 30, $CH_2$), 2.60–2.70 (m, 2, $CH_2$ epoxypropyl), 2.75–3.10 (m, 6, $CH_2$ epoxypropyl), 3.20–3.30 (m, 2, epoxypropyl CH), 3.55–3.75 (t, 2, $CH_2$), 7.10–7.25 (m, 1, aromatic), 7.40–7.60 (m, 2, aromatic).

EXAMPLE 7

PREPARATION OF 4-TOLUIC ACID: 2,6-DI(2,3-EPOXYPROPYL PHENYL ETHER

4-Toluyl chloride (3.09 gm, 0.02 mol) was diluted with 1,2-dichloromethane (50 ml) and added to a solution of triethylamine (4 ml) and 2,6-diallylphenol (3.48 gm, 0.02 mol) in 1,2-dichloromethane (40 ml) at room temperature. After the addition was complete, the reaction mixture was refluxed for 1 hr, cooled and the organic solution washed with water (2×), dried over MgSO4 and evaporated to give 4-toluic acid: 2,6-diallylphenyl ester. MS m/z 292 (M+ calcd for $C_{20}H_{20}O_2$=292). H NMR(300 MHz, $CDCl_3$) d 2.50(s, 3, $CH_3$), 3.20–3.35 (d, 4, $CH_2$), 5.00–5.15 (m, 4, $CH_2$, vinyl), 5.85–6.10 (m, 2, CH vinyl), 8.20–8.40 (m, 2, aromatic). Oxidation of the product as described in Example 1 gave 4-toluic acid: 2,6-(2,3-epoxypropyl)phenyl ester. MS m/z 324 (M+ calcd for $C_{20}H_{20}O_4$=324). H NMR (300 MHz, $CDCl_3$) d 2.50 (s, 3, $CH_3$), 2.40–2.50 (m, 2, $CH_2$ epoxypropyl), 2.65–2.95 (m, 6, $CH_2$ epoxypropyl), 3.25–3.45 (m, 2, CH epoxypropyl) 7.35–7-75 (m 5, aromatic), 8.21–8.40 (d, 2, aromatic).

EXAMPLE 8

PREPARATION OF 4-TOLUENESULFONIC ACID: 2,6-DI(2,3-EPOXYPROPYL)PHENYL ESTER

Triethylamine (4 ml) and 4-toluenesulfonyl chloride (3.80 gm, 0.02 mol) were diluted with 1,2-dichloromethane (50 ml) and 2,6-diallylphenol (3.48 gm, 0.02 mol), dissolved in 1,2-dichloromethane (10 ml), was added drop wise to the phenol-triethylamine solution at room temperature and then refluxed for 1 hr. The reaction mixture was cooled, washed with water and dried over $MgSO_4$, filtered and evaporated to give 4-toluenesulfonic acid: 2,6-diallylphenyl ester as an oil. Purification was carried out via filtering a hexane solution of the ester through silica gel. MS m/z 328 (M+ calcd for $C_{19}H_{20}O_3S$=328). H NMR (300 MHz, $CDCl_3$) d 2.50 (s, 3, $CH_3$), 3.25–3.35 (d, 4, $CH_2$), 4.95–5.10 (m, 4, $CH_2$ vinyl), 5.75–5.90 (m, 2, CH, vinyl), 7.10–7.25 (m, 3, aromatic), 7.85–7.95 (m, 2, aromatic). Oxidation of product as described in Example 1 gave 4-toluenesulfonic acid 2,6-di (2,3-epoxypropyl)phenyl ester. MS m/z 360 (M+ calcd for $C_{19}H_{20}O_5S$=360. H NMR (300 MHz, $CDCl_3$) d 2.45–2.55 (m, 2, $CH_2$ epoxypropyl), 2.50 (s, 3, $CH_3$), 2.35–2.95 (m, 6, $CH_2$ epoxypropyl), 3.21–3.35 (m, 2, CH epoxypropyl), 7.25–7.45 (m, 5, aromatic), 7.85–7.95 (d, 2, aromatic).

EXAMPLE 9

PREPARATION OF 2,6-DI(2,3-EPOXYPROPYL)PHENYL METHYL CARBONATE 2,6-Diallylphenol (3.48, 0.02 mol) and triethylamine (4 ml) was diluted with 1,2-dichloromethane (50 ml). Methyl chloroformate (2.00 gm, 0.027 mol) was diluted with 1,2-dichloromethane (10 ml) and added drop wise to the phenol-amine solution. After the addition was complete, the reaction was refluxed for 1 hr, cooled and poured onto water. The organic layer was washed with water (2×) dried over $MgSO_4$ and evaporated to give 2,6-diallylphenyl methyl carbonate. MS m/z 232 (M+ calcd for $C_{15}H_{16}O_3$=232). H NMR (300 MHz, $CDCl_3$) d 3.30–3.40 (d, 4. $CH_2$), 3.90 (s, 3, $CH_3$), 5.05–5.20 (m, 4, $CH_2$ vinyl), 5.85–6.00 (m, 2, CH vinyl), 7.10–7.27 (m, 3, aromatic). Oxidation of the product as described in Example 1 gave 2,6-di(2,3-epoxypropyl)phenyl methyl carbonate as an oil. MS m/z 264 (M+ calcd for $C_{14}H_{16}O_5$=264). H NMR (300 MHz, $CDCl_3$) d 2.60–2.70 (m, 2, $CH_2$ epoxypropyl), 2.40–2.90 (m, 6, $CH_2$ epoxypropyl), 3.25–3.40 (m, 2, $CH_2$ epoxypropyl), 3.85 (s, 3, $OCH_3$), 7.30–7.65 (m, 3, aromatic).

EXAMPLE 10

PREPARATION OF 2,6-(2,3-EPOXYPROPYL)PHENYL DIETHYL PHOSPHATE 2,6-Diallylphenol (3.16 gm, 0.018 mol) was diluted with toluene(50 ml) and sodium hydroxide (0.72 gm, 0.018 mol) added to the solution. The reaction flask was equipped with a Dean and Stark apparatus and refluxed for 1 hr to remove water and to form an anhydrous solution of the phenate salt. After cooling, diethyl chlorophosphate, (3.45 gm) was added and the solution stirred overnight. Filtration of the solids and evaporation of the toluene gave 2,6-diallylphenyl diethyl phosphate. MS m/z 310. (M+ calcd for $C_{16}H_{23}PO_4$=310). H NMR (300 MHz, $CDCl_3$) d 1.30–1.45 (t, 6, $CH_3$), 3.66–3.72 (d, 4, $CH_2$), 4.20–4.49 (m, 4, $OCH_2$), 5.15–5.30 (m, 4, $CH_2$ vinyl), 5.90–6.16 (m, 2, CH vinyl), 7.20 7.30 (m, 3, aromatic). Oxidation of the product as described in Example 1 gave 2,6-(2,3-epoxypropyl)phenyl diethyl phosphate. MS m/z 342 (M+ calcd for $C_{16}H_{23}PO_6$=342). H NMR (300 MHz, $CDCl_3$) d 3.65 (t, 6, $CH_3$), 2.55–2.65 (m, 2, $CH_2$ epoxypropyl), 2.75–2.85 (m, 2, $CH_2$ epoxypropyl), 2.90–3.30 (m, 4, $CH_2$ epoxypropyl), 3.40–3.55 (m, 2, CH epoxypropyl), 4.10–4.35 (m, 4, $OCH_2$), 7.05–7.25 (m, 1, aromatic), 7.40–7.60 (m, 2, aromatic).

EXAMPLE 11

PREPARATION OF 2,2-{3-(2,3-EPOXYPROPYL)-4-METHOXYPHENYL}PROPANE

Bis-A {2,2-bis-(4-hydroxyphenyl) propane} was converted to the diallyl ether via reaction of the diphenate salt with allyl chloride. The diallyl ether of Bis-A was heated in refluxing o-dichlorobenzene for 48 hrs to yield 2,2-bis(3-allyl4-hydroxyphenyl)propane. MS m/z 308 (M+ calcd for $C_{21}H_{24}O_2$=308). The diphenol was converted to the dimethyl ether via reaction with methyl iodide as described in Example 2. MS m/z 336 (M+ calcd for $C_{23}H_{28}O_2$=336). H NMR (300 MHz, $CDCl_3$) d 1.70 (s, 6, $CH_3$), 3.37 (m, 4, $CH_2$ allyl), 3.82 (s, 6, $OCH_3$), 4.92–5.05 (m, 4, $CH_2$ vinyl), 5.85–6.15 (m, 2, vinyl), 6.70–7.05 (m, 6, aromatic). Oxidation of the diallyl derivative as described in Example 1 gave 2,2-{bis(3,3-epoxypropyl)4-methoxyphenyl}propane. MS m/z 353 (M+ —$CH_3$) {Calcd for $C_{23}H_{28}O_4$=368}. H NMR (300 MHz, $CDCl_3$) d 1.60 (s, 6, $CH_3$), 2.25 (d, 2, $CH_2$epoxypropyl) 2.60–2.75 (m, 4, $CH_2$ epoxypropyl), 2.85–2.95 (m, 2, $CH_2$ epoxypropyl), 3.15–3.22 (m, 2, CH epoxypropyl) 3.83 (s, 6, $OCH_3$), 6.75 (d, 2, aromatic), 7.10 (d, 4, aromatic).

EXAMPLE 12

PREPARATION OF 4-METHOXY-3-(2,3-EPOXYPROPYL)PHENYL SULFONE 4,4*-Sulfonyldiphenol (25 gm, 0.10 mol) was dissolved in methanol (200 ml) and sodium hydroxide (8.0 gm, 0.20 mol) was added and stirred until the solution was homogeneous. Allyl chloride (20 mL 0.25 mol) was added and the solution heated and stirred at ~45° C. until the reaction was complete. The reaction was poured onto water and extracted with ethyl acetate. The organic extract was washed with water (2×), dried, recrystallized from aqueous acetone to give 4-alloxyphenyl sulfone, mp 140–142° C. MS m/z 330 (M+ calcd for $C_{18}H_{18}O_4S$=330). H NMR (300 MHz,$CDCl_3$) d 4.56 (d, 4, $OCH_2$), 5.27–5.44 (m, 4, vinyl), 5.93–6.08 (m, 2, CH vinyl), 6.95 (d, 4, aromatic), 7.82 (d, 4, aromatic). 4-Allylphenyl sulfone (19.5 gm, 0.59 mol) was refluxed in o-dichlorobenzene for 60 hrs (weekend) to give after solvent evaporation and recrystallization from hexane -1,2-dichloromethane gave 3-allyl-4-hydroxyphenyl sulfone, mp 154–156 C. MS m/z 330 (M+ calcd for $C_{18}H_{18}O_4S$=330). H NMR (300 MHz, DMSO-d 6) d 3.30 (d, 4, $CH_2$) 5.20 (d, 4, vinyl), 5.91–6.00 (m, 2, vinyl), 6.85 (d, 1, aromatic), 7.57 (d, 2, aromatic). 3-Allyl-4-hydroxyphenyl sulfone (4.5 gm, 0.0134 mol) was dissolved in dimethylacetamide (25 ml) and powdered sodium hydroxide added to generate the diphenate salt. When the solution was homogeneous, methyl iodide (3.87 gm, 0.028 mol) was added and the reaction mixture heated at ~40° C. for 40 hr. The reaction was poured onto hexane. The hexane solution was washed with water (3×), dried over $MgSO_4$ and the solvent evaporated to give 4-methoxy-3-allylphenyl sulfone mp 82–85 C. MS m/z 358 (M+ calcd for $C_{20}H_{22}O_4S$=358). H NMR (300 MHz, $CDCl_3$) d 3.35 (d, 2, aromatic), 3.85 (s, 3, $CH_3$), 4.85–5.10 (m, 4, $CH_2$ vinyl), 5.85–6.10 (m, 2, CH vinyl), 6.88 (d, 2, aromatic), 7.65–7.80 (m, 3, aromatic). 4-Methoxy-3-allylphenyl sulfone (2.0 g, 0.0056 mol) was oxidized as described in Example 1 to give 4-methoxy-3-(2,3-epoxypropyl)phenyl sulfone, mp 105–108° C. MS m/z 390 (M+ calcd for $C_{20}H_{22}O6S$=390). H NMR (300 MHz, $CDCl_3$) d 2.53 (t, 2, $CH_2$), 2.76 (t, 2, $CH_2$), 2.80–2.97 (m, 4, $CH_2$), 3.85 (s, 6, $OCH_3$), 6.92 (d, 2, aromatic), 7.72–7.85 (m, 2, aromatic).

What is claimed is:
1. Diepoxide esters or ethers having the formulas:

(I)

(II)

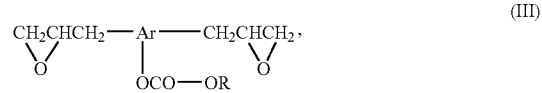

(III)

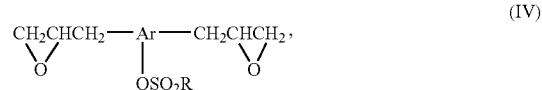

(IV)

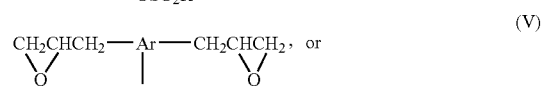

(V)

-continued

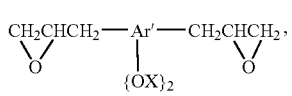
(VI)

where Ar is a trivalent aromatic radical of 6–20 carbon atoms, Ar' is a bridged diaromatic radical having the formula Ar—Y—Ar and Y is O, CO, S, SO$_2$, —(CH$_2$)y , or —C(R")$_2$— and y is from 0 to 6, and R and R' are the same or different alkyl, alkylene aryl, aryl, arylene alkyl, alkylene alkoxy, alkylene aryloxy, arylene alkoxy and arylene aryloxy radical having from 6–20 carbon atoms, X is —R, —COR, —COOR, —SO$_2$R, PORR' and R" is methyl.

2. The diepoxide ethers of claim 1 having the formula

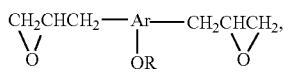

where Ar is a trivalent aromatic radical of 6–20 carbon atoms and R is an alkyl, alkylene aryl, aryl, arylene alkyl, alkylene alkoxy, alkylene aryloxy, arylene alkoxy and arylene aryloxy radical having from 6–20 carbon atoms.

3. The diepoxide carboxylic acid esters of claim 1 having the formula

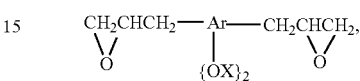

where Ar is a trivalent aromatic radical of 6–20 carbon atoms and R is an alkyl, alkylene aryl, aryl, arylene alkyl, alkylene alkoxy, alkylene aryloxy, arylene alkoxy and arylene aryloxy radical having from radical of 6–20 carbon atoms.

4. The diepoxide carbonic acid esters of claim 1 having the formula

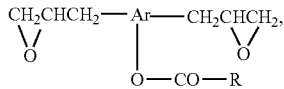

where Ar is a trivalent aromatic radical of 6–20 carbon atoms and R is an alkyl, alkyl aryl, aryl, aryl alkyl, alkylene alkoxy, alkylene aryloxy, arylene alkoxy and arylene aryloxy radical having from 6–20 carbon atoms.

5. The diepoxide sulfonic acid esters of claim 1 having the formula

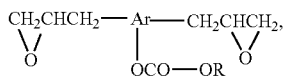

where Ar is a trivalent aromatic radical of 6–20 carbon atoms and R is an alkyl, alkylene aryl, aryl, arylene alkyl, alkylene alkoxy, alkylene aryloxy, arylene alkoxy or arylene aryloxy radical having from 6–20 carbon atoms.

6. The diepoxide phosphorus esters of claim 1 having the formula

where Ar is a trivalent aromatic carbon radical of 6–20 carbon atoms and R and R' are alkyl, alkylene aryl, aryl, arylene alkyl, alkylene alkoxy, alkylene aryloxy, arylene alkoxy and arylene aryloxy radicals having from 6–20 carbon atoms.

7. The diepoxide esters of claim 1 having the formula

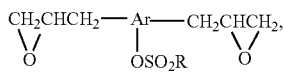

where Ar' is a bridged diaromatic radical having the formula Ar—Y—Ar and Y is O, CO, S, SO$_2$, —(CH$_2$)y , or —C(R")$_2$— and y is from 0 to 6, Ar is a trivalent aromatic radical of 6–20 carbon atoms, and R and R' are the same or different alkyl, alkylene aryl, aryl, arylene alkyl, alkylene alkoxy, alkylene aryloxy, arylene alkoxy and arylene aryloxy radical having from 6–20 carbon atoms, X is —R, —COR, —COOR, —SO$_2$R, or —PORR' and R" is methyl.

8. The diepoxide of claim 2 where the ether is 2,6-di-(2,3-epoxypropyl)phenyl methyl ether.

9. The diepoxide of claim 2 where the ether is 2,6-di-(2,3-epoxypropyl)phenyl ethyl ether.

10. The diepoxide of claim 2 where the ether is 4-methyl-2,6-di-(2,3-epoxypropyl)phenyl methyl ether.

11. The diepoxide of claim 2 where the ether is 2,6-di(2,3-epoxypropyl)phenyl benzyl ether.

12. The diepoxide of claim 2 where the ether is 2,6-di(2,3-epoxypropyl)phenyl-4-cyano phenyl ether.

13. The diepoxide of claim 2 where the ether is 2,6-di(2,3-epoxypropyl)phenyl octadecyl ether.

14. The diepoxide of claim 3 where the ester is 4-toluic acid: 2,6-di(2,3-epoxypropyl)phenyl ester.

15. The diepoxide of claim 4 where the ester is 2,6-di(2,3-epoxypropyl)phenyl methyl carbonate.

16. The diepoxide of claim 5 where the ester is 4-toluenesulfonic acid: 2,6-di(2,3-epoxypropyl)phenyl ester.

17. The diepoxide of claim 6 where the ester is 2,6-di(2,3-epoxypropyl)phenyl diethyl phosphate.

18. The diepoxide of claim 7 where the diether is 2,2-{3-(2,3-epoxypropyl)-4-methoxyphenyl}propane.

19. The diepoxide of claim 7 where the diether is 3(2,3-epoxypropyl)-4-methoxyphenyl sulfone.

20. The diepoxide ethers of claim 1 having the formula

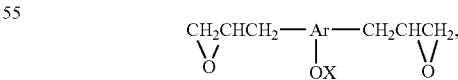

where Ar is a trivalent aromatic radical of 6–20 carbon atoms and X is —R, —COR, —COOR, —SO$_2$R, PORR' and R and R' are the same or different alkyl, alkylene aryl, aryl, arylene alkyl, alkylene alkoxy, alkylene aryloxy, arylene alkoxy and arylene aryloxy radical having from 6–20 carbon atoms.

* * * * *